United States Patent [19]

Winn et al.

[11] 4,044,135
[45] Aug. 23, 1977

[54] ANTIHYPERTENSIVE AGENTS

[75] Inventors: Martin Winn, Deerfield; Jaroslav Kyncl, Lake Bluff; Daniel Ambrose Dunnigan, Winthrop Harbor; Peter Handley Jones, Lake Forest, all of Ill.

[73] Assignee: Abbott Laboratories, North Chicago, Ill.

[21] Appl. No.: 621,979

[22] Filed: Oct. 14, 1975

[51] Int. Cl.² ............... C07D 239/84; A61K 31/505
[52] U.S. Cl. .......................... 424/251; 260/256.4 Q
[58] Field of Search ............. 260/256.4 Q, 256.4 B; 424/251

[56] References Cited

U.S. PATENT DOCUMENTS 3,920,636   11/1975   Takahashi et al. ........... 260/256.4 Q Primary Examiner—Paul M. Coughlan, Jr.
Attorney, Agent, or Firm—Gildo E. Fato; Robert L. Niblack

[57] ABSTRACT

Described are the compounds 2[4(tetrahydro-2-furoyl)-hexahydro-1,4-diazepinyl-1]-4-amino-6,7-dimethoxy quinazoline and pharmaceutically acceptable acid addition salts thereof. The compounds are useful as antihypertensive agents.

6 Claims, No Drawings

ANTIHYPERTENSIVE AGENTS

BACKGROUND OF THE INVENTION

A recently introduced drug, 2-[4-(2-furoyl)-1-piperazine-1-yl]-4-amino-6,7-dimethoxyquinazoline, commonly identified by the generic name prazosin, is a hypotensive drug producing peripheral arterial dilation. This drug is represented by the formula:

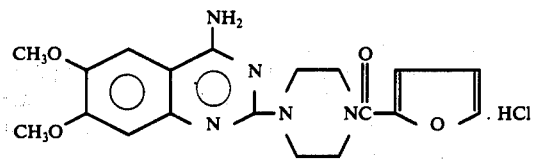

I

This drug however, as reported in The Lancet, May 10, 1975, at page 1095, exhibits significant toxicity and can cause a profound fall in blood pressure. Sudden collapse with loss of consciousness for periods ranging from a few minutes to one hour following use of this drug have been reported. (The Lancet and British Medical Journal, June 28, 1975, pages 727, 728). The drug prazosin also has a very low solubility and it is therefore postulated that the problem of toxicity sometimes resulting upon oral administration of this drug may be caused by erratic absorption.

SUMMARY OF THE INVENTION

This invention relates to compounds consisting of 2[4-(tetrahydro-2-furoyl)-hexahydro-1,4-diazepinyl-1]-4-amino-6,7-dimethoxy quinazoline and pharmaceutically acceptable acid addition salts thereof, represented by the following formula:

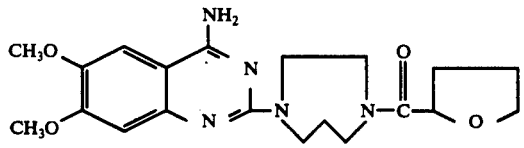

II

The compounds of this invention are useful as antihypertensive agents and have a solubility of over 100 times that of prazosin. Because of their considerable water solubility, these compounds can be administered intravenously, particularly for emergency purposes and should be adsorbed uniformly by all patients. Further, they can be administered in time release form as well as parenterally, including intravenously.

DETAILED DESCRIPTION

The compounds of the present invention are prepared according to the following reaction scheme:

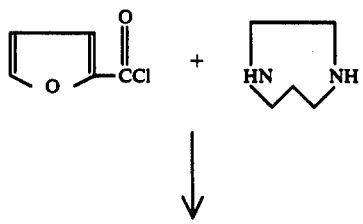

Example 1

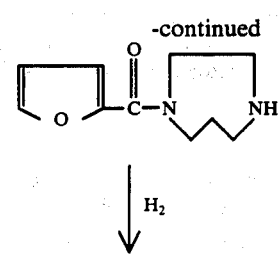

Example 2

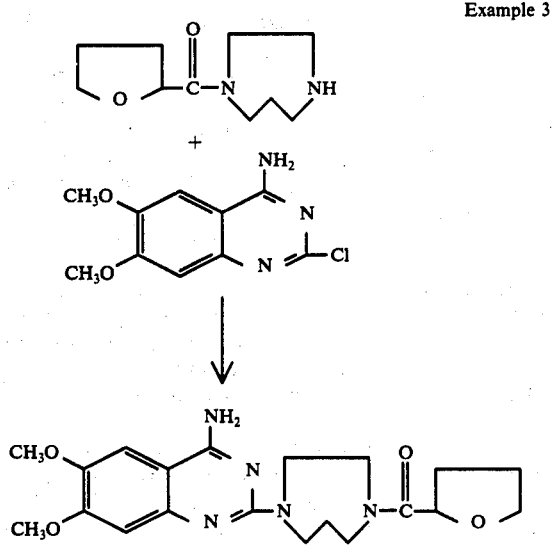

Example 3

In the illustrated reactions, the compound of Formula II is prepared by reacting hexahydro-1,4-diazepine with furoyl chloride in an acid solution. The resultant 1-(2-furoyl)-hexahydro-1,4-diazepine is hydrogenated to produce 1-(tetrahydro-2-furoyl)-hexahydro-1,4-diazepine which is reacted with 2-chloro-4-amino-6,7-dimethoxyquinazoline in the presence of methoxy ethanol to give the compound 2-[4-(tetrahydro-2-furoyl)-hexahydro-1,4-diazepinyl-1]-4-amino-6,7-dimethoxy quinazoline. The hydrochloride salt is prepared by acidifying with hydrogen chloride.

The compounds of this invention are useful as antihypertensive agents. The compounds are effective at dosages generally 0.1 to 100 milligrams daily.

EXAMPLE 1

1-(2-Furoyl)-Hexahydro-1,4-Diazepine 70 g. hexahydro-1,4-diazepine was dissolved in 160 ml. water. Hydrochloric acid (20%) was added until the pH was 5.5. Using a pH meter to keep the pH between 4.5 and 5.5, 79.5 g. furoyl chloride was added in portions along with 25% sodium hydroxide. After addition, 50% sodium hydroxide was added to raise the pH to 9.5. The solution was extracted with chloroform 4 times, the chloroform extracts dried over anhydrous potassium carbonates and the solution distilled giving 53.24 g. product. b.p. 125° - 130°

Analysis Calculated For: $C_{10}H_{14}N_2O_2$
Theory: C = 61.83  H = 7.27  N = 14.42
Found: C = 61.57  H = 7.39  N = 14.30

EXAMPLE 2

1-(Tetrahydro-2-Furoyl)-7-Hexahydro-1,4-Diazepine 33.0 g. of 1-(2-furoyl)-hexahydro-1,4-diazepine was dissolved in 200 ml. ethanol and 8 g. of 5% rhodium or carbon added. The mixture was hydrogenated at 3 atmospheres. The catalyst was filtered and the liquid distilled to give 31.0 g. product. b.p. 138° – 140°/0.8Mm $N_D^{25} = 1.5179$

EXAMPLE 3

2-[4-Tetrahydro-2-Furoyl)-Hexahydro-1,4-Diazepinyl-1]-4-Amino-6,7-Dimethoxy Quinazoline Hydrochloride To 5.10 g. 2-chloro-4-amino-6,7-dimethoxy quinazoline U.S. 3,635,979, Example 1, Column 10, in 50 ml. 2-methoxy ethanol was added 9.50 g. 1-(tetrahydro-1-furoyl)-hexahydro-1,4diazipine. The mixture was refluxed for 3 hours. The solution was concentrated in vacuo and the residue was treated with potassium bicarbonate in water, the solid which formed was filtered, washed with water and dissolved in ethanol. The solution was acidified with hydrogen chloride and cooled to give 9.05 g. product. m.p. 286° – 288°

The solubility of the hydrochloride salt of the compound of formula II was found by adding water to 27.0 milligrams of the compound in a vial, drop by drop, until a clear solution was formed. 0.312 grams of water was required. The solubility was calculated as 87 milligrams per milliliter of water. In contrast, the compound of formula I was found to have a solubility of 0.67 mg./ml.

The advantageous solubility of the described compounds facilitate their administration parenterally, particularly intravenously as well as their formulation, with pharmaceutically acceptable carriers, into compositions for oral administration.

The antihypertensive activity of the hydrochloride salt of the compound of formula II was determined, in the manner described in copending application Ser. No. 621,980, filed Oct. 14, 1975, by administering the compound to spontaneously hypertensive (SH) rats and measuring the percent change in blood pressure. The results are summarized as follows:

| | % CHANGE IN BLOOD PRESSURE* | | | |
|---|---|---|---|---|
| | 1 Hour | 3 Hours | 5 Hours | 24 Hours |
| Oral Dose 1 Mg./Kg. | −31,−26 | −29,−27 | −18,−10 | −5,−10 |
| Intraperitoneal Administration 30 Mg./Kg. | −30,−37 | −27,−30 | −25,−25 | −0,−0 |

*2 SH Rats

What is claimed is:

1. The compound comprising 2[4-(tetrahydro-2-furoyl)-hexahydro-1,4-diazepinyl-1]-4-amino-6,7-dimethoxy quinazoline and pharmaceutically acceptable salts thereof.

2. The compound of claim 1: 2[4-tetrahydro-2-furoyl)-hexahydro-1,4-diazepinyl-1]-4-amino-6,7-dimethoxy quinazoline hydrochloride.

3. A composition for the treatment of hypertension comprising a therapeutically effective amount of a compound comprising 2[4-(tetrahydro-2-furoyl)-hexahydro-1,4-diazepinyl-1]-4-amino-6,7-dimethoxy quinazoline or a pharmaceutically acceptable salt thereof, and a pharmaceutically acceptable carrier.

4. The composition of claim 3 wherein the compound is 2[4-(tetrahydro-2-furoyl)-hexahydro-1,4-diazepinyl-1]-4-amino-6,7-dimethoxy quinazoline hydrochloride.

5. The method of treating hypertension in mammals comprising administering to said mammals a therapeutically effective amount of a compound of claim 1.

6. The method of claim 5 wherein the compound is 2[4-(tetrahydro-2-furoyl)-hexahydro-1,4-diazepinyl-1]-4-amino-6,7-dimethoxy quinazoline hydrochloride.

* * * * *